(12) United States Patent
Fukami et al.

(10) Patent No.: US 6,258,837 B1
(45) Date of Patent: Jul. 10, 2001

(54) NEUROPEPTIDE Y RECEPTOR ANTAGONIST

(75) Inventors: Takehiro Fukami; Takahiro Fukuroda; Akio Kanatani; Masaki Ihara; Takayoshi Okabe, all of Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/403,031
(22) PCT Filed: Apr. 22, 1998
(86) PCT No.: PCT/JP98/01855
§ 371 Date: Dec. 8, 1999
§ 102(e) Date: Dec. 8, 1999
(87) PCT Pub. No.: WO98/47505
PCT Pub. Date: Oct. 29, 1998

(30) Foreign Application Priority Data

Apr. 23, 1997 (JP) .................................................. 9-120310

(51) Int. Cl.$^7$ ............................ A01N 43/16; A61K 31/35
(52) U.S. Cl. ............................................................. 514/454
(58) Field of Search ............................................... 514/454

(56) References Cited

U.S. PATENT DOCUMENTS

| | | | |
|---|---|---|---|
| 3,414,587 | 12/1968 | Lehr et al. | 260/335 |
| 3,454,577 | 7/1969 | Lehr et al. | 260/279 |
| 3,536,757 | 10/1970 | Lehr et al. | 260/556 |
| 3,539,590 | 11/1970 | Oftedahl | 260/335 |

FOREIGN PATENT DOCUMENTS

| | | |
|---|---|---|
| 49-125364 | 11/1974 | (JP) . |
| WO 99/15516 | 4/1999 | (WO) . |
| WO 99/27965 | 6/1999 | (WO) . |

OTHER PUBLICATIONS

Baldas et al., "The Mass–Spectra of Dimedon Derivatives of Aldehydes", Tetrahedron Lett., (11), 1331–1355, 1968.*
Solomons et al., Organic Chemistry, Third Edition, p. 373–374, copyright 1984.*
J.R. Dimmock, et al., Eur. J. Med. Chem., vol. 23, pp. 111–117, "Evaluation of Mannich Bases of 2–arylidene–1, 3–diketones versus Murine P388 Leukemia", 1988.
L. Jurd, J. Organic Chemistry, vol. 31, No. 5, pp. 1639–1641, "Anthocyanidins and Related Compounds. IX. The Synthesis of 9–phenacyl–5–ketotetrahydroxanthenes", May, 1966.
J. Baldas, et al., Tetrahedron Letters, No. 11, pp. 1531–1355, "The Mass–Spectra of Dimedone Derivatives of Aldehydes", 1968.

* cited by examiner

Primary Examiner—Dwayne C. Jones
(74) Attorney, Agent, or Firm—Oblon, Spivak, McClelland, Maier & Neustadt, P.C.

(57) ABSTRACT

The present invention relates to a neuropeptide Y receptor antagonist comprising a compound represented by the formula [I]:

[I]

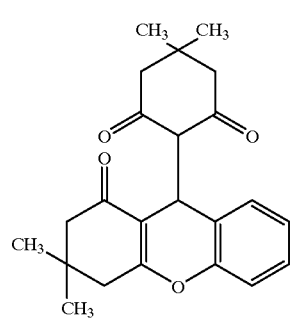

as an active ingredient.

4 Claims, No Drawings

NEUROPEPTIDE Y RECEPTOR ANTAGONIST

CROSS-REFERENCE TO RELATED APPLICATIONS

This application is a national-stage filing under 35 U.S.C. 371 of PCT/JP98/01855, filed Apr. 22, 1998.

FIELD OF THE INVENTION

The present invention is useful in the field of medicines. More specifically, medicines containing compounds represented by the formula [I] of the present invention as active ingredients are useful as neuropeptide Y receptor antagonists and as agents for the treatment of various diseases of circulatory organs, central nervous system and metabolic system.

BACKGROUND OF THE INVENTION

Neuropeptide Y (hereinafter abbreviated as NPY) is a peptide consisting of 36 amino acids, which was isolated from porcine brain for the first time by Tatemoto et al. in 1982 [Nature, vol.296, p.659 (1982)]. NPY is broadly distributed in central and peripheral nervous systems and has various in vivo functions as one of the peptides most abundantly present in the nervous systems. That is, in the central nervous system, NPY acts as an aperitive and significantly promotes a fat accumulation associated with the lowering of a basal metabolism via secretion of various hormones and actions of the nervous systems. It is known that a continuous intracerebroventricular administration of NPY induces obesity and insulin resistance based on the above actions. And, it is known that in rodents showing hereditary or dietary obesity, NPY concentration in the brain is increased. Further, the increase in expression of the NPY receptor is reported. NPY is also associated with the control of mood and functions of the central autonomic nervous system. In addition, in the peripheral nervous system, NPY is present together with norepinephrine in the sympathetic nerve terminal and associated with the tension of the sympathetic nervous system [International Journal of Obesity, vol.19, p.517 (1995); Endocrinology, vol.133, p.1753 (1993); Neuropeptide Y and drug development, p.15 (1997); Brain Research, vol.744, p.1 (1997); The biology of neuropeptide Y, p.315 (1993)].

The function of NPY is expressed when it is bound to an NPY receptor present in the central or peripheral nervous system. Therefore, the expression of the function of NPY can be prevented if the binding of NPY to the NPY receptor is inhibited. Consequently, it is expected that compounds capable of antagonizing the binding of NPY to the NPY receptor are useful in the prevention or treatment of various diseases associated with NPY, for example, diseases of circulatory organs such as hypertension, nephropathy, cardiopathy and angiospasm; diseases of central nervous system such as bulimia, depression, epilepsy and dementia; metabolic diseases such as obesity, diabetes and dysendocrisiasis, or glaucoma [Trends in Pharmacological Sciences, vol.15, p.153 (1994)].

Compounds structurally similar to the compounds related to the present invention are disclosed in Eur. J. Med. Chem., vol.23, No.2, p.111 (1988); J. Organic Chemistry, vol.31, No.5, p.1639 (1966); JP-49125364A; U.S. Pat. Nos. 3,414,587, 3,454,577, 3,536,757 and 3,539,590; and etc. Especially, J. Organic Chemistry, vol.31, No.5, p.1639 (1966) clearly discloses the compound related to the present invention.

However, an antagonistic action to NPY of the compound in question is not described at all therein.

DISCLOSURE OF THE INVENTION

An object of the present invention is to provide a new medicine having an antagonistic action to NPY.

The present inventors have found that a compound represented by the formula [I]:

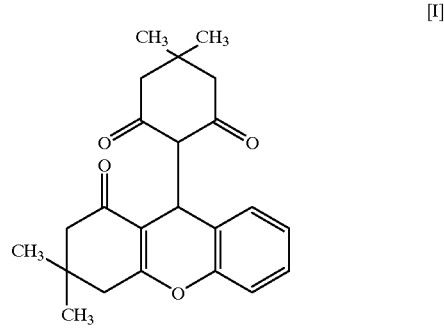

[I]

has an antagonistic action to NPY.

Since the compound [I] related to the present invention has the antagonistic action to NPY, it is useful as an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma.

Especially, the compound [I] related to the present invention is useful as an agent for the treatment of bulimia, obesity, diabetes or the like.

The present invention relates to a neuropeptide Y receptor antagonist and an agent for the treatment of bulimia, obesity or diabetes comprising the compound represented by the formula [I] as an active ingredient.

The term "agent for the treatment" as used herein means a drug to be used for the treatment and/or prevention of various diseases.

Although the compounds represented by the formula [I] may exists in optical isomers or tautomers, all of the optical isomers and tautomers and their mixtures are also included in the present invention.

As the above tautomer, the compound represented by the formula [I-1]:

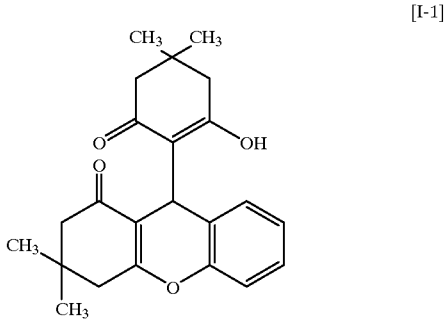

[I-1]

can be exemplified.

The compound related to the present invention can be prepared by, for example, the method as described in the aforementioned publication (J. Organic Chemistry, vol. 31, No.5, p.1639 (1966)) or the method as illustrated in the following Preparation Examples.

An optically active compound represented by the formula [I] can be prepared by passing a racemate corresponding thereto through an optically active column or by adding an optically active amine such as cinchonidine to the racemate to form a salt and then subjecting to the fractional recrystllization.

The usefulness of the compound related to the present invention as a medicine is demonstrated by showing its antagonistic activity to NPY in the following pharmacological test examples.

Pharmacological Test Example 1 (test of inhibition of NPY binding)

cDNA Sequence encoding a human NPY Y5 receptor [International Publication WO 96/16542] was cloned into expression vectors pcDNA3, pRc/RSV (manufactured by Invitrogen) and pCI-neo (manufactured by Promega). Using the cationic lipid method [see Proceedings of the National Academy of Science of the United States of America, vol.84, p.7413 (1987)], host cells COS-7, CHO and LM(tk-) (American Type Culture Collection) were transfected with the thus prepared expression vectors to obtain cells in which the NPY Y5 receptor had been expressed.

Each of the membrane preparations thus prepared from the cells in which the NPY Y5 receptor had been expressed was incubated together with each compound to be tested and 20,000 cpm of [$^{125}$I] peptide YY (manufactured by Amersham) at 25° C. for 2 hours in an assay buffer solution (25 mM HEPES buffer, pH 7.4, containing 10 mM magnesium chloride, 1 mM phenylmethylsulfonyl fluoride and 0.1% bacitracin) and then, the reaction mixture was filtered through a glass filter GF/C. After washing with 50 mM Tris buffer, pH 7.4, containing 0.3% BSA, radioactivity on the glass filter was measured using a gamma counter. Non-specific binding was measured in the presence of 1 μM of peptide YY to calculate a concentration of each compound to be tested which concentration is needed to inhibit 50% of the specific binding of the peptide YY ($IC_{50}$ value) [see Endocrinology, vol.131, p.2090 (1992)]. As the result, $IC_{50}$ value of the compound was calculated to be 27 nM.

As shown in the above, the compound related to the present invention strongly inhibited the binding of the peptide YY (a homologue of NPY) to the NPY Y5 receptor.

Pharmacological Test Example 2 (test of inhibition of feeding behavior induced by bPP)

Under pentobarbital anesthesia (single intraperitoneal injection of 50 mg/kg), a chronic guide cannula (outer diameter 0.8 mm; inner diameter 0.5 mm; length 10 mm) was stereotactically inserted in a right lateral cerebral ventricle of each of SD male rats (7 to 8-week-old; 200 to 300 g) and fixed using a dental resin. A tip of the guide cannula was positioned 0.9 mm behind a bregma, 1.2 mm at the right of a median line and in the depth of 1.5 mm from the brain surface. An inner needle was inserted such that its tip projected from the tip of the guide cannula by about 2 mm and arrived to a lateral cerebral ventricle. After a recovery period of about one week, a bovine pancreatic polypeptide (bpp, 5 μg/head/10 μl) was administered to the lateral cerebral ventricle. A compound to be tested was orally administered one hour before the administration of bpp and food intake during two hours from the administration was measured. In this connection, the compound to be tested was administered after dissolving in a 0.5% aqueous methyl cellulose solution and bpp was administered after dissolving in 10 mM phosphate buffered saline.

The compound of the present invention significantly inhibits the increase in food intake induced by bPP (a homologue of NPY).

Pharmacological Test Example 3 (acute toxicity test)

A compound to be tested in an amount of 500 mg/kg was orally administered to each of SD male rats (10-week-old; 300 to 400 g). After immediately, 5 minutes, 30 minutes, 1 hour, 2 hours, 4 hours, 6 hours, 8 hours and 24 hours from the administration, the condition of each rat was observed. And, after 24 hours from the administration, the rat was killed by dehematizing via carotid artery and then laparotomized in order to observe the presence or absence of any change in abdominal organs by the naked eye. In this connection, the compound to be tested was administered in a dose of 5 ml/kg after suspending in a 0.5% aqueous methyl cellulose solution.

At any time until 24 hours after the administration of the compound to be tested, no abnormality in general health of each rat was observed. And, abdominal organs were observed to be unchanged.

In consequence, the compound related to the present invention is useful as an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma, especially bulimia, obesity and diabetes.

The compound related to the present invention can be administered orally or parenterally and by formulating into any dosage form suitable for such an administration, it can be used as an agent for the treatment of the diseases of circulatory organs such as hypertension, nephropathy, cardiopathy and angiospasm, the diseases of central nervous system such as bulimia, depression, epilepsy and dementia, the metabolic diseases such as obesity, diabetes and dysendocrisiasis, or glaucoma. In clinical use of the compound related to the present invention, it is also possible to administer the compound after formulating it into various dosage forms by adding any pharmaceutically acceptable additive(s). Examples of such additive include those which are generally used in the field of pharmaceuticals such as gelatin, lactose, sucrose, titanium oxide, starch, crystalline cellulose, hydroxypropylmethyl cellulose, carboxymethyl cellulose, corn starch, microcrystalline wax, white soft paraffine, magnesium aluminate methasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinyl pyrrolidone, magnesium stearate, light anhydrous silicic acid, talc, vegetable oil, benzyl alcohol, gum arabic, propylene glycol, polyalkylene glycol, cyclodextrin and hydroxypropyl cyclodextrin.

Examples of the dosage form to be formulated as a mixture with these additives include solid preparations such as tablet, capsule, granule, powder or suppository; and liquid preparations such as syrup, elixir or injection, which can be prepared in accordance with any conventional method in the field of pharmaceuticals. In this connection, in the case of the liquid preparation, it may be in a form which is dissolved or suspended in water or other suitable solvent in time of use. Also, particularly in the case of an injection, it may be dissolved or suspended in physiological saline or glucose solution if necessary or further mixed with buffer and/or preservative.

The pharmaceutical preparation may contain the compound related to the present invention in an amount of from 1.0 to 100% by weight, preferably from 1.0 to 60% by weight, with respect to the total preparation. These pharmaceutical preparations may also contain any other therapeutically effective compounds.

When the compound related to the present invention is, for example, clinically used, its dosage and the number of times of its administration vary depending on the sex, age, body weight and the conditions of the patient and the nature and ranges of the intended therapeutic effects and the like. When it is administered to an adult, it is desirable in general to orally administer in an amount of from 0.1 to 100 mg/kg per day by dividing the daily dose into 1 to several times per day, or to parenterally administer in an amount of from 0.001 to 10 mg/kg by dividing the daily dose into 1 to several times per day.

As described above, the present invention can provide an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma, especially an agent for the treatment of bulimia, obesity, diabetes or the like. Of course, the present invention can also provide the new method for the treatment of the above diseases using them.

BEST MODE FOR CARRYING OUT THE INVENTION

The present invention is described further in detail with reference to the following examples, but the invention should in no aid way be restricted thereby.

EXAMPLE 1

10 Parts of the compound represented by the formula [I], 15 parts of heavy magnesium oxide and 75 parts of lactose are uniformly mixed to make a powdery or particulate preparation having the diameter of 350 μm or less. This preparation is filled in capsules to obtain capsules.

EXAMPLE 2

45 Parts of the compound represented by the formula [I], 15 parts of starch, 16 parts of lactose, 21 parts of crystalline cellulose, 3 parts of polyvinyl alcohol and 30 parts of distilled water are uniformly mixed, and the mixture is granulated, dried and sieved to obtain granules having the diameter of 1410 to 177 μm.

EXAMPLE 3

Granules are made in the same manner as that described in Example 2. Then, 96 parts of the granules are mixed with 3 parts of calcium stearate and the mixture is compressed to obtain tablets having the diameter of 10 mm.

EXAMPLE 4

90 Parts of granules made in the same manner as that described in Example 2 are mixed with 10 parts of crystalline cellulose and 3 parts of calcium stearate and the mixture is compressed to obtain tablets having the diameter of 8 mm, to which a suspension of syrup, gelatin and precipitated calcium carbonate is added to obtain sugar coated tablets.

EXAMPLE 5

0.6 Part of the compound represented by the formula [I], 2.4 parts of a nonionic surfactant and 97 parts of a saline are mixed with heating, and the mixture is filled in ampuls and sterilized to obtain injections.

Preparation Example 1

Preparation of 3,3-dimethyl-9-(4,4-dimethyl-2,6-dioxo-cyclohexyl)-1-oxo-1,2,3,4-tetrahydroxanthene (compound of formula [I])

1.83 Grams of salicyl aldehyde and 4.21 g of dimedone were suspended in 22.5 ml of acetic acid and 30 ml of water and the suspension was stirred at 100° C. for 1.5 hours. The reaction mixture was allowed to cool to room temperature. The precipitated solid was filtered to obtain 5.06 g of the title compound as a colorless powder. Yield =92%.

m.p. =210–212° C.

$^1$H-NMR (CDCl$_3$) δ: 0.99 (3H, s), 0.99 (3H, s), 1.03 (3H, s), 1.12 (3H, s), 1.92 (1H, d, J=16.5 Hz), 2.00 (1H, d, J=16.5 Hz), 2.33 (2H, s), 2.37 (2H, s), 2.47 (1H, d, J=17.7 Hz), 2.60 (1H, d, J=17.7 Hz), 4.67 (1H, s), 7.00–7.04 (3H, m), 7.13–7.19 (1H, m), 10.47 (1H, brs).

Preparation Example 2

Preparation of (+) and (−)-3,3-dimethyl-9-(4,4-dimethyl-2,6-dioxo-cyclohexyl)-1-oxo-1,2 3,4-tetrahydroxanthene ((+)- and (−)-isomers of compound of formula [I])

100 Miligrams of the racemic compound of the formula [I] was dissolved in 10 ml of isopropanol, and the solution was injected in an optically active column for preparative high performance liquid chromatography (CHIRALPAK AD; 5 cmID×50 cmL, particle size 20 μm). This column was eluted with hexane/isopropanol (9:1) at the rate of 100 ml/min. The eluate was detected under UV ray of 236 nm. Relatively initial fractions were collected and concentrated under reduced pressure to obtain 26 mg of the (−)-isomer of the compound of the formula [I] as a white solid. $[\alpha]_D^{20}$=−182° (c=1.000, 1=5.0, CHCl$_3$).

Relatively late fractions were collected and concentrated under reduced pressure to obtain 19 mg of the (+)-isomer of the compound of the formula [I] as a white solid. $[\alpha]_D^{20}$=+191° (c=1.000, 11=5.0, CHCl$_3$).

Preparation Example 3

Preparation of (S)-3,3-dimethyl-9-(4,4-dimethyl-2,6-dioxo-cyclohexyl)-1-oxo-1,2 ,3,4-tetrahydroxanthene ((S)-isomer of compound of formula [I])

The racemic compound of the compound of the formula [I] (5g, 13.66 mmol) and cinchonidine (4.02 g, 13.66 mmol) were suspended in 350 ml of acetonitrile, stirred with heating and dissolved. After the solution was allowed to cool to room temperature and then allowed to stand overnight, the produced precipitates were collected by filtration. A part of the precipitates were suspended in chloroform and a 10% aqueous citric acid solution and stirred vigorously to dissolve. After the organic layer was separated, the aqueous layer was re-extracted with chloroform. The organic layer and the extract were combined, washed with a 10% aqueous citric acid solution and dried over anhydrous sodium sulfate. After the solvent was distilled away, an amorphous crude product was obtained. This crude product was dissolved in a minimum amount of methanol without heating and allowed to stand overnight in a refrigerator to prepare crystals. The crystals were filtered to obtain the (S)-isomer of the compound of the formula [I] as a crystalline solid.

Optical purity as determined by HPLC (CHIRALPAK AD column; hexane/isopropanol (9:1) was 99.5%.

m.p.=172–174° C.

$[\alpha]_D^{20}$=+191° (c=1.000, 1=5.0, CHCl$_3$).

Absolute configuration was confirmed by analyzing the cinchonidine salt using X-ray crystallography.

INDUSTRIAL APPLICABILITY

Since the compound related to the present invention has an antagonistic action to NPY, it is useful as an agent for the treatment of various diseases associated with NPY, for example, diseases of circulatory organs such as hypertension, nephropathy, cardiopathy and angiospasm, diseases of central nervous system such as bulimia, depression, epilepsy and dementia, metabolic diseases such as obesity, diabetes and dysendocrisiasis, or glaucoma.

What is claimed is:

1. A method for effecting neuropeptide Y antagonism in a mammal in need thereof, which comprises administering to said mammal an effective amount of a compound represented by the formula I:

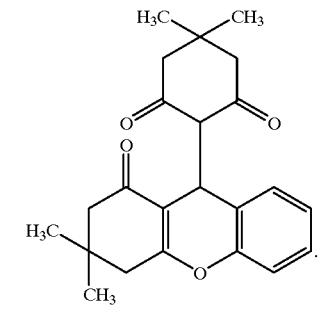

(I)

2. A method for treating and/or preventing of a disease associated with neuropeptide Y in a mammal in need thereof, which comprises administering to said mammal an effective amount of a compound represented by the formula I:

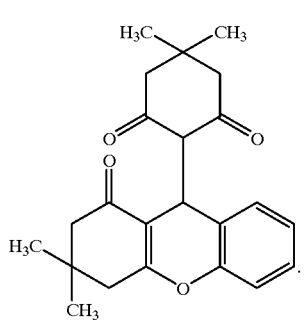

(I)

3. The method of claim 2, wherein the disease associated with neuropeptide Y is hypertension, nephropathy, cardiopathy, angiospasm, bulimia, depression, epilepsy, dementia, obesity, diabetes, dysendocrisiasis, glaucoma or a combination thereof.

4. The method of claim 2, wherein the disease associated with neuropeptide Y is bulimia, obesity or diabetes or a combination thereof.

* * * * *